United States Patent
Lehmann et al.

(10) Patent No.: US 7,094,905 B2
(45) Date of Patent: Aug. 22, 2006

(54) PROCESS FOR THE HYDROGENATION OF C—C DOUBLE BONDS

(75) Inventors: Stefan Lehmann, Ober-Klingen (DE); Thomas Koppe, Schaffhausen (CH)

(73) Assignee: Merck Patent GmbH, Darmstadt (DE)

( * ) Notice: Subject to any disclaimer, the term of this patent is extended or adjusted under 35 U.S.C. 154(b) by 295 days.

(21) Appl. No.: 10/363,136

(22) PCT Filed: Aug. 9, 2001

(86) PCT No.: PCT/EP01/09203

§ 371 (c)(1),
(2), (4) Date: Mar. 6, 2003

(87) PCT Pub. No.: WO02/20442

PCT Pub. Date: Mar. 14, 2002

(65) Prior Publication Data

US 2004/0030150 A1 Feb. 12, 2004

(30) Foreign Application Priority Data

Sep. 6, 2000 (DE) ................................ 100 43 957
Jul. 21, 2001 (DE) ................................ 101 35 681

(51) Int. Cl.
*C07D 235/00* (2006.01)
(52) U.S. Cl. .................................................. 548/302.7
(58) Field of Classification Search .............. 548/302.7
See application file for complete search history.

(56) References Cited

U.S. PATENT DOCUMENTS 4,792,625 A 12/1988 Wiener et al.

FOREIGN PATENT DOCUMENTS

EP 0570824 11/1993

OTHER PUBLICATIONS

Database Crossfire Beilstein 'Online! Beilstein Institut Zur Foerderung der Chemischen Wissenschaften, Frankfurt am Main, DE; Database accession No. 852627 (reaction ID), XP002186069; Reaction Details 3; & R. J. Bonilla et al., Chem. Commun., 2000, pp. 941-942, No. 11.
Database Crossfire Beilstein 'Online! Beilstein Institut Zur Foerderung der Chemischen Wissenschaften, Frankfurt am Main, DE; Database accession No. 8678322 (reaction ID), XP002186070, & M. A. Nazareno et al., Molecules, 2000, pp. 589-590, vol. 5, No. 3.

*Primary Examiner*—Kamal A. Saeed
(74) *Attorney, Agent, or Firm*—Millen, White, Zelano, Branigan, P.C.

(57) ABSTRACT

The present invention relates to a gentle process for catalytic hydrogenation and to a process for the preparation of biotin using the hydrogenation step. The process according to the invention for the selective, catalytic hydrogenation of a C—C double bond on a thiazole ring system having at least one functional group which can be converted into a salt under basic conditions is characterised in that the hydrogenation is carried out in a protic solvent is a pH>7.

22 Claims, No Drawings

PROCESS FOR THE HYDROGENATION OF C—C DOUBLE BONDS

The present invention relates to a gentle process for catalytic hydrogenation, and to a process for the preparation of biotin using the hydrogenation step.

In established syntheses of biotin, an intermediate containing a double bond is hydrogenated on the thiolane ring. This selective hydrogenation of the double bond is usually carried out with metal catalysis. This reaction is usually carried out in organic solvents.

Thus, European Patent EP-B-0 273 270 describes a synthesis of biotin in which a hydrogenation is carried out in accordance with Equation I. The solvent used here is preferably isopropanol.

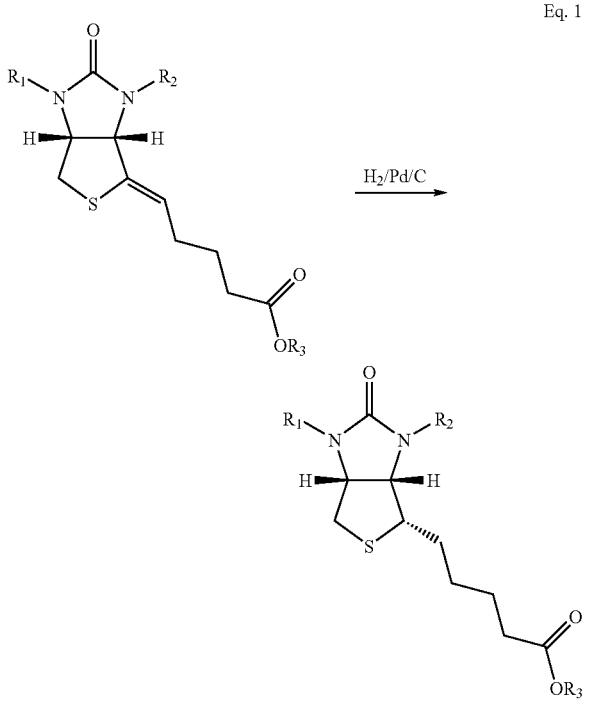

Eq. 1

In these formulae, $R_1$ is a phenylethyl group, $R_2$ is a hydrogen, acetyl, propionyl, benzoyl, benzyl, ethoxycarbonyl, tert-butoxycarbonyl, benzyloxycarbonyl, phenoxycarbonyl, p-methoxybenzyl, methoxymethyl, pyranyl, benzenesulfonyl, p-toluenesulfonyl, methylsulfonyl, diphenylphosphinyl, diethoxyphosphinyl, trimethylsilyl or a butyldimethylsilyl radical, and $R_3$ is selected from H and $C_{1-4}$-alkyl.

Other applications describe modified hydrogenation conditions: for example, European Patent Application EP-A-0 633 263 describes hydrogenation using a soluble Pd catalyst, preferably dichlorobis(benzonitrile)palladium or palladium acetate, in a solvent mixture comprising water and at least one alcohol. In the process described in Japanese Patent Application JP-A-07330776, the hydrogenation is carried out using palladium acetate in isopropanol. On use of soluble catalysts of this type, separation of the catalyst from the product is often difficult and in each case requires an additional step. European Patent Application EP-A-0 780 392 is concerned with the problem of separating soluble catalysts of this type from the reaction mixture. It is proposed to add, when the reaction is complete, a polymeric flocculant, which precipitates the catalyst from the solution, and to filter off the precipitate.

In spite of these various known variants for carrying out the hydrogenation process, there continues to be a demand for alternative hydrogenation processes which are simple to carry out, inexpensive and fast and can be integrated well into the chain of other synthetic steps. The processes must ensure high selectivity and high degrees of conversion.

It is particularly advantageous if successive reaction steps can be carried out in the same solvent. A complex solvent change with purification and drying steps of the intermediates is then unnecessary.

In the case of the synthesis of biotin, this means that it appears desirable to be able to carry out the hydrogenation in the medium in which the thieno[3,4-d]imidazol-4-ylidenepentanoic acid is formed.

In conventional syntheses of biotin—as described, for example, in International Patent Application WO 95/26965—the thieno[3,4-d]imidazol-4-ylidenepentanoic acid is formed in protic solvents, often in an aqueous extraction solution. However, this intermediate is not soluble in pure water, and consequently water appeared unsuitable as solvent for the further reaction.

It has surprisingly now been found that, given a suitable setting of the pH, it is possible to carry out the hydrogenation directly in this protic solvent.

A first subject-matter of the present invention is accordingly a process for the catalytic hydrogenation of at least one C—C double bond in a compound containing at least one functional group which can be converted into a salt under basic conditions, in which the hydrogenation is carried out in a protic solvent at a pH of >7.

In accordance with the invention, the double bond is preferably located on a thiazole ring system. For the purposes of the present invention, a thiazole ring system is taken to mean a ring system comprising one or more, preferably fused rings which contains at least one nitrogen heteroatom and at least one sulfur heteroatom. The rings here can be saturated or unsaturated.

The at least one double bond to be hydrogenated can be one or more double bonds in the ring system and/or one or more double bond directly adjacent to rings of the system.

For the purposes of the invention, the term at least one functional group which can be converted into a salt under basic conditions is taken to mean a group which is in charged form under the selected hydrogenation conditions. The carboxyl or hydroxyl functions are preferably, it being particularly preferred in accordance with the invention for at least one carboxyl function to be present. The functional group which can be converted into a salt under basic conditions is in accordance with the invention bonded to the thiazole ring system either directly or via one or more side chains.

If a new chiral centre is formed by the hydrogenation, the process is preferably carried out in such a way that the hydrogenation takes place enantioselectively. The person skilled in the art in this area is presented with no difficulties at all in correspondingly selecting the hydrogenation conditions, in particular catalyst, pressure and temperature, in such a way that enantioselective hydrogenation takes place.

In a preferred variant of the process according to the invention, the thiazole ring system is a thiolane ring system, where the term thiolane ring system (tetrahydrothiophene derivative) is taken to mean a ring system which contains at least one substituted or unsubstituted thiolane ring which is preferably bonded, preferably fused, to at least one further ring. For the purposes of the present invention, sulfur-containing cyclopentane ring systems containing double bonds are expressly also referred to as thiolane ring systems.

In a preferred embodiment of the process, the thiolane ring system is present in a compound of the formula I

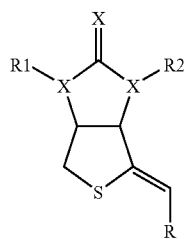

I in which the radicals R1 and R2 are a protecting group, X is O or S, and R is selected from the group comprising the radicals $C_{1-20}$-hydroxyalkyl, $C_{1-20}$-carboxyalkyl and the esters of hydroxyl or carboxyalkyl radicals of this type.

The protecting groups R1 and R2 in the formula I are preferably selected from the group comprising the radicals acetyl, propionyl, benzoyl, benzyl, phenylethyl, ethoxycarbonyl, tert-butoxycarbonyl, benzyloxycarbonyl, phenoxycarbonyl, p-methoxybenzyl, methoxymethyl; pyranyl, benzenesifonyl, p-toluenesulfonyl, methylsulfonyl, diphenylphosphinyl, diethoxyphosphinyl, trimethylsilyl, trifluoroacetyl, methoxycarbonyl, allyloxycarbonyl, trifluorophenyl and butyldimethylsilyl radical, where R1 and R2 are preferably identical and are particularly preferably benzyl or phenylethyl radicals.

Suitable solvents are protic solvents, in particular the conventional protic solvents known to the person skilled in the art, such as water, lower alcohols, such as, for example, methanol, ethanol and isopropanol, and primary and secondary amines and mixtures of protic solvents of this type, it being particularly preferred for the solvent employed to be water.

In accordance with the invention, the hydrogenation is carried out at a pH of >7 and preferably at a pH of <10. It is likewise preferred for a pH in the range from 8 to 9, in particular in the range from 8.5 to 8.9, to be set in the reaction medium, it having proven particularly advantageous for a pH of about 8.7 to be set.

The pH here is preferably set with the aid of a weak base, such as, for example, sodium carbonate or potassium carbonate, a corresponding buffer system which acts in the weakly alkaline range, or an alkali or alkaline earth metal hydroxide, such as sodium hydroxide solution or potassium hydroxide solution. However, other bases which are familiar to the person skilled in the art can also be employed here.

Suitable catalysts for the hydrogenation are all common homogeneous and heterogeneous catalysts, the catalyst employed is particularly preferably at least one noble metal, preferably selected from the elements Pt, Pd and Rh, or a transition metal, such as Mo, W, Cr, but particularly Fe, Co and Ni, either individually or in the form of a mixture. The catalysts or catalyst mixtures here can also be employed on supports, such as activated carbon, aluminium oxide or kieselguhr. The metal here can also be employed in the form of the Raney compound, for example Raney nickel. If the catalysis is carried out in a homogeneous process, it is preferred for the catalyst employed to be one or more complex compounds of the said metals, such as, for example, Wilkinson's catalyst [chlorotris(triphenylphosphine)-rhodium]. In a preferred variant of the present invention, we employed a heterogeneous catalyst, it being particularly preferred for the catalyst employed in the process according to the invention to be Pd, preferably on activated-carbon support, for example 5% by weight of Pd on C.

The hydrogenation is usually carried out at a temperature in the range from 20–150° C., preferably in the range from 70 to 120° C. and particularly preferably at about 100° C. The hydrogenation is furthermore advantageously carried out at a hydrogen pressure of from 1 to 200 bar, preferably from 1 to 10 bar and particularly preferably at from about 3 to 5 bar.

A further advantage of the process according to the invention is the ease of separation of the hydrogenation product from the hydrogenation solution. In a preferred variant of the process according to the invention, the hydrogenation product is isolated by a pH shift. A pH in the range from 1 to 7, preferably around 6, is preferably set here. The pH shift can preferably be achieved here by addition of an organic acid or of a mineral acid, preferably hydrochloric acid. After the pH shift has taken place, the product is in this variant of the invention preferably extracted with an organic solvent. Suitable organic solvents are esters, such as, in particular, ethyl acetate and butyl acetate, ethers, such as, in particular, diethyl ether, MTB ether methyl tetrahydrofuran and tetrahydrofuran, ketones, such as, in particular, ethyl propyl ketone, dichloromethane, chloroform, carbon tetrachloride, aliphatic hydrocarbons, such as, in particular, pentane, hexane and heptane, aromatic hydrocarbons, such as benzene, toluene and xylene and isomer mixtures thereof, where xylene is particularly preferably employed.

The process is particularly preferably employed as an intermediate step in the preparation of biotin, in particular of (+)-biotin. It is therefore particularly preferred for the group X in the formula I to be an oxygen atom and for the radical R in the formula I to be a butyric acid radical, which may be in esterified form.

A further subject-matter of the present invention is accordingly a process for the preparation of biotin in which the hydrogenation according to the invention is employed.

The chemical synthesis of biotin is known from the literature and can be carried out, for example, as described in European Patent EP-B-0 273 270. Modified syntheses and routes starting from other starting materials (for example L-cysteine or L-cystine see DE-A-36 13 245) are also known to the person skilled in the art, and consequently he is presented with absolutely no difficulties in replacing the hydrogenation step in a biotin synthesis known per se with the hydrogenation process described in this invention.

It is particularly preferred for the thieno[3,4-d]imidazol-4-ylidenepentanoic acid to be hydrogenated in the same protic solvent in which the reaction step taking place immediately before the hydrogenation took place. As already stated above, the reaction step preceding the hydrogenation carried out in conventional processes for the preparation of biotin is purification of the the thieno[3,4-d]imidazol-4-ylidenepentanoic acid using water. In this embodiment of the present invention, water is therefore a particularly preferred solvent.

A preferred variant of the process according to the invention is described in detail below:

When carrying out the hydrogenation according to the invention in the synthesis of biotin, the thieno[3,4-d]imidazol-4-ylidenepentanoic acid protected on the nitrogen atoms is preferably firstly dissolved in water. This is particularly preferably carried out by alkalisation using a weak base, such as, for example, aqueous sodium hydroxide solution. A pH in the range 8–9, in particular in the range 8.5–8.9, is preferably set, it having proven particularly advantageous for a pH of 8.7 to be set.

The metal catalyst, preferably palladium on carbon support (for example 5% Pd/C), is subsequently added. 20–30% by weight, particularly preferably 25% by weight, of the catalyst, based on the amount of starting material, are preferably added.

The hydrogenation is carried out at a temperature in the range 20–150° C., preferably in the range from 70 to 120° C. and particularly preferably at about 60° C., and a hydrogen pressure of from 1 to 200 bar, preferably from 1 to 10 bar and particularly preferably at from about 3 to 5 bar.

The hydrogenation product is preferably isolated by a pH shift, where a pH of about 6 is preferably set using hydrochloric acid. After the pH shift has taken place, the product is in this variant of the invention extracted with an organic solvent, preferably xylene.

An example of the performance of the preferred variant of the process according to the invention described here is indicated below.

EXAMPLE 1

(3aS, 6aR)Hexahydro2-Oxo-1,3-Dibenzylthieno[3,4-d]Imidazol-4-Ylpentanoic Acid 100 g of (3aS, 6aR)hexahydro2-oxo-1,3-dibenzylthieno[3,4-d]imidazol-4-ylidenepentanoic acid (formula I) are dissolved in 340 ml of water at 40° C., where the pH is set to 8.7 using aqueous sodium hydroxide solution. 25% by weight of 5% Pd/C are added to the solution. The mixture is subsequently hydrogenated at an $H_2$ pressure of 3 bar and 100° C. until the takeup of hydrogen is complete. The catalyst is filtered off after cooling. The solution is set to pH=6.0 using hydrochloric acid and extracted with 300 ml of xylene. The aqueous phase is subsequently extracted again with 100 ml of xylene. The organic phases are combined, and the solvents are evaporated, leaving 96 g of (3aS, 6aR)-hexahydro-2-oxo-1,3-dibenzylthieno[3,4-d]imidazol-4-ylpentanoic acid (formula II) as a pale-yellow oil.

Yield: 95.5% of theory

Characterisation: spectroscopic data correspond to the literature values.

What is claimed is:

1. A process for the catalytic hydrogenation of at least one C—C double bond present in a compound of the formula I

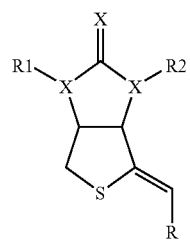

wherein each of the radicals R1 and R2 is a protecting group, X is O or S, and R is $C_{1-20}$-hydroxyalkyl or an ester thereof, or $C_{1-20}$-carboxyalkyl or an ester thereof comprising hydrogenating in a protic solvent at a pH of >7 and in $H_2$ gas at a hydrogen pressure of 1–200 bar.

2. A process according to claim 1, wherein the solvent is water.

3. A process according to claim 1, wherein a pH of 8–9 is set in the reaction medium.

4. A process according to claim 1, wherein the pH is set with the aid of a weak base, a corresponding buffer system which acts in the weakly alkaline range, or an alkali or alkaline earth metal hydroxide.

5. A process according to claim 1, wherein R1 and R2 in the formula I are, independently, acetyl, propionyl, benzoyl, benzyl, phenylethyl, ethoxycarbonyl, tert-butoxycarbonyl, benzyloxycarbonyl, phenoxycarbonyl, p-methoxybenzyl, methoxymethyl, pyranyl, benzenesulfonyl, p-toluenesulfonyl, methyl-sulfonyl, diphenyiphosphinyl, diethoxyphosphinyl, trimethylsilyl, trifluoroacetyl, methoxycarbonyl, allyloxycarbonyl, trifluorophenyl or butyldimethylsilyl radical.

6. A process according to claim 1, wherein the catalyst is a noble metal, or a transition metal.

7. A process according to claim 1, wherein the hydrogenation is carried out at 20–150° C.

8. A process according to claim 1, wherein the hydrogenation is carried out at a hydrogen pressure of 1–10 bar.

9. A process according to claim 1, wherein a hydrogenation product is isolated by a pH shift.

10. A process according to claim 1, wherein the group X in the formula I is an oxygen atom and/or the radical R in the formula I is a butyric acid radical, optionally esterified.

11. A process for the catalytic enantioselective hydrogenation of at least one C—C double bond located on or in a thiazole ring system containing at least one functional group which can be converted into a salt under basic conditions, comprising hydrogenating in a protic solvent at a pH of >7 and at a hydrogen pressure of 1–200 bar.

12. A process according to claim 11, wherein the thiazole ring system is a thiolane ring system.

13. A process according to claim 8, wherein R1 and R2 are identical.

14. A process according to claim 6, wherein the catalyst is Pd on an activated-carbon support.

15. A process according to claim 3, wherein the pH is 8.5–8.9.

16. A process according to claim 5, wherein R1 and R2 are benzyl or phenylethyl.

17. A process according to claim 9, further comprising setting the pH at 1–7 to provide the pH shift.

18. A process according to claim 9, further comprising extracting with an organic solvent.

19. A process according to claim 1, wherein R1 is a phenylethyl group, R2 is a hydrogen, acetyl, propionyl, benzoyl, benzyl, ethoxycarbonyl, tert-butoxycarbonyl, benzyloxycarbonyl, phenoxycarbonyl, p-methoxybenzyl, methoxymethyl, pyranyl, benzenesulfonyl, p-toluenesulfonyl, methylsulfonyl, diphenyiphosphinyl, diethoxyphosphinyl, trimethylsilyl or a butyldimethylsilyl radical, and R is of the formula:

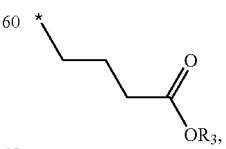

where $R_3$ is H or $C_{1-4}$ alkyl.

20. A process according to claim 1, wherein R is a butyric acid radical or an esterified butyric acid radical.

21. A process according to claim 1, wherein R contains at least one functional group that can be converted into a salt under basic conditions.

22. A process according to claim 1, wherein no solvent other than the protic solvent is present during the hydrogenation.

* * * * *

UNITED STATES PATENT AND TRADEMARK OFFICE
CERTIFICATE OF CORRECTION

PATENT NO. : 7,094,905 B2
APPLICATION NO. : 10/363136
DATED : August 22, 2006
INVENTOR(S) : Lehmann et al.

It is certified that error appears in the above-identified patent and that said Letters Patent is hereby corrected as shown below:

Column 6, line 14 reads "diphenyiphosphinyl," should read -- diphenylphosphinly --
Column 6, line 37 reads "according to claim 8" should read -- according to claim 5 --
Column 6, line 55 reads "diphenyiphosphinyl," should read -- diphenylphosphinly --

Signed and Sealed this

Thirteenth Day of February, 2007

JON W. DUDAS
*Director of the United States Patent and Trademark Office*